US012616550B2

(12) United States Patent
Jeon et al.

(10) Patent No.: US 12,616,550 B2
(45) Date of Patent: May 5, 2026

(54) MEDICAL THREE-DIMENSIONAL IMAGE MEASURING DEVICE AND MEDICAL IMAGE MATCHING SYSTEM

(71) Applicant: KOH YOUNG TECHNOLOGY INC, Seoul (KR)

(72) Inventors: Moon Young Jeon, Seongnam-si (KR); Seung Yeol Ryu, Gunpo-si (KR)

(73) Assignee: KOH YOUNG TECHNOLOGY INC, Seoul (KR)

( * ) Notice: Subject to any disclaimer, the term of this patent is extended or adjusted under 35 U.S.C. 154(b) by 305 days.

(21) Appl. No.: 18/248,854

(22) PCT Filed: Oct. 13, 2021

(86) PCT No.: PCT/KR2021/014108
§ 371 (c)(1),
(2) Date: Apr. 12, 2023

(87) PCT Pub. No.: WO2022/080855
PCT Pub. Date: Apr. 21, 2022

(65) Prior Publication Data
US 2023/0380927 A1 Nov. 30, 2023

(30) Foreign Application Priority Data

Oct. 13, 2020 (KR) ........................ 10-2020-0131865

(51) Int. Cl.
*A61B 90/00* (2016.01)
*A61B 34/20* (2016.01)
*G06T 7/246* (2017.01)

(52) U.S. Cl.
CPC ............ *A61B 90/361* (2016.02); *A61B 34/20* (2016.02); *A61B 90/39* (2016.02); *G06T 7/246* (2017.01);
(Continued)

(58) Field of Classification Search
CPC .. A61B 2017/00991; A61B 2034/2046; A61B 2034/2048; A61B 2034/2055;
(Continued)

(56) References Cited

U.S. PATENT DOCUMENTS

| | | | |
|---|---|---|---|
| 10,512,508 | B2 | 12/2019 | Rohling et al. |
| 2005/0113659 | A1 | 5/2005 | Pothier et al. |

(Continued)

FOREIGN PATENT DOCUMENTS

| | | |
|---|---|---|
| CN | 106714681 | 5/2017 |
| CN | 110325141 | 10/2019 |

(Continued)

OTHER PUBLICATIONS

Extended European Search Report for European Application No. 21880502.6, dated Feb. 27, 2024.

(Continued)

*Primary Examiner* — Zhiyu Lu
(74) *Attorney, Agent, or Firm* — KILE PARK REED & HOUTTEMAN PLLC

(57) ABSTRACT

A medical three-dimensional image measuring device includes a light source configured to output light, a camera configured to generate three-dimensional image information by receiving reflected light generated by reflecting the light from an object, a housing including the camera disposed therein and forming an opening through which the reflected light enters into the housing, and a marker disposed on the housing to be capable of changing at least one of a relative location or a relative posture to the opening and including a tracking surface configured to be imaged by an external imaging device for tracking a location and a posture.

16 Claims, 10 Drawing Sheets

(52) U.S. Cl.
CPC ................ *A61B 2034/2046* (2016.02); *A61B 2090/3945* (2016.02); *G06T 2200/04* (2013.01)

(58) Field of Classification Search
CPC .... A61B 2034/2059; A61B 2034/2065; A61B 2090/309; A61B 2090/3618; A61B 2090/3945; A61B 34/20; A61B 5/0064; A61B 5/1127; A61B 90/361; A61B 90/39; G01B 11/002; G01B 11/26; G06T 2200/04; G06T 7/246
See application file for complete search history.

(56) References Cited

U.S. PATENT DOCUMENTS

| | | | |
|---|---|---|---|
| 2012/0092461 A1 | 4/2012 | Fisker et al. | |
| 2013/0060146 A1 | 3/2013 | Yang et al. | |
| 2015/0054922 A1 | 2/2015 | Fisker et al. | |
| 2016/0035108 A1 | 2/2016 | Yu et al. | |
| 2016/0360954 A1 | 12/2016 | Rohling et al. | |
| 2017/0245946 A1 | 8/2017 | Tabandeh et al. | |
| 2017/0272726 A1* | 9/2017 | Ovsiannikov | G01C 25/00 |
| 2018/0046835 A1* | 2/2018 | Hong | G01S 7/481 |
| 2018/0064497 A1 | 3/2018 | Hussain et al. | |
| 2018/0068441 A1 | 3/2018 | Yu et al. | |
| 2018/0153626 A1 | 6/2018 | Yang et al. | |
| 2018/0255293 A1 | 9/2018 | Fisker et al. | |
| 2019/0124323 A1 | 4/2019 | Fisker et al. | |
| 2019/0200006 A1 | 6/2019 | Fisker et al. | |
| 2019/0289283 A1 | 9/2019 | Fisker et al. | |
| 2020/0008881 A1 | 1/2020 | Marti et al. | |
| 2020/0015911 A1 | 1/2020 | Yi | |
| 2020/0169722 A1 | 5/2020 | Fisker et al. | |
| 2020/0234434 A1 | 7/2020 | Yu et al. | |
| 2020/0281660 A1 | 9/2020 | Homan et al. | |
| 2020/0345428 A1 | 11/2020 | Marti et al. | |
| 2021/0211638 A1 | 7/2021 | Fisker et al. | |
| 2021/0306617 A1 | 9/2021 | Fisker et al. | |
| 2022/0151710 A1 | 5/2022 | Marti et al. | |
| 2023/0380927 A1 | 11/2023 | Jeon et al. | |
| 2024/0058076 A1 | 2/2024 | Marti et al. | |

FOREIGN PATENT DOCUMENTS

| | | |
|---|---|---|
| CN | 110461270 | 11/2019 |
| JP | 2010-054320 | 3/2010 |
| JP | 2012-530267 | 11/2012 |
| JP | 2019-501704 | 1/2019 |
| JP | 2023-545450 | 10/2023 |
| WO | 2011/134083 | 11/2011 |
| WO | 2016/114834 | 7/2016 |
| WO | 2019/130314 | 7/2019 |

OTHER PUBLICATIONS

Office Action with English translation for Japanese Patent Application No. 2023-522567, dated Apr. 23, 2024.
Korean Office Action with English translation for Korean Patent Application or Patent No. 10-2020-0131865, dated Nov. 29, 2021.
Written Opinion, with English translation, corresponding to International Application No. PCT/KR2021/014108, dated Jan. 24, 2022.
Korean Office Action with English translation for Korean Patent Application No. 10-2022-0113372, dated May 30, 2023.
Japanese Office Action dated Sep. 29, 2025, in Japanese Patent Application No. 2024-160215 [including English machine translation].
Chinese Office Action dated Jan. 26, 2026, in Chinese Patent Application No. 2026012600745600 [including English machine translation].

* cited by examiner

Figure 1:
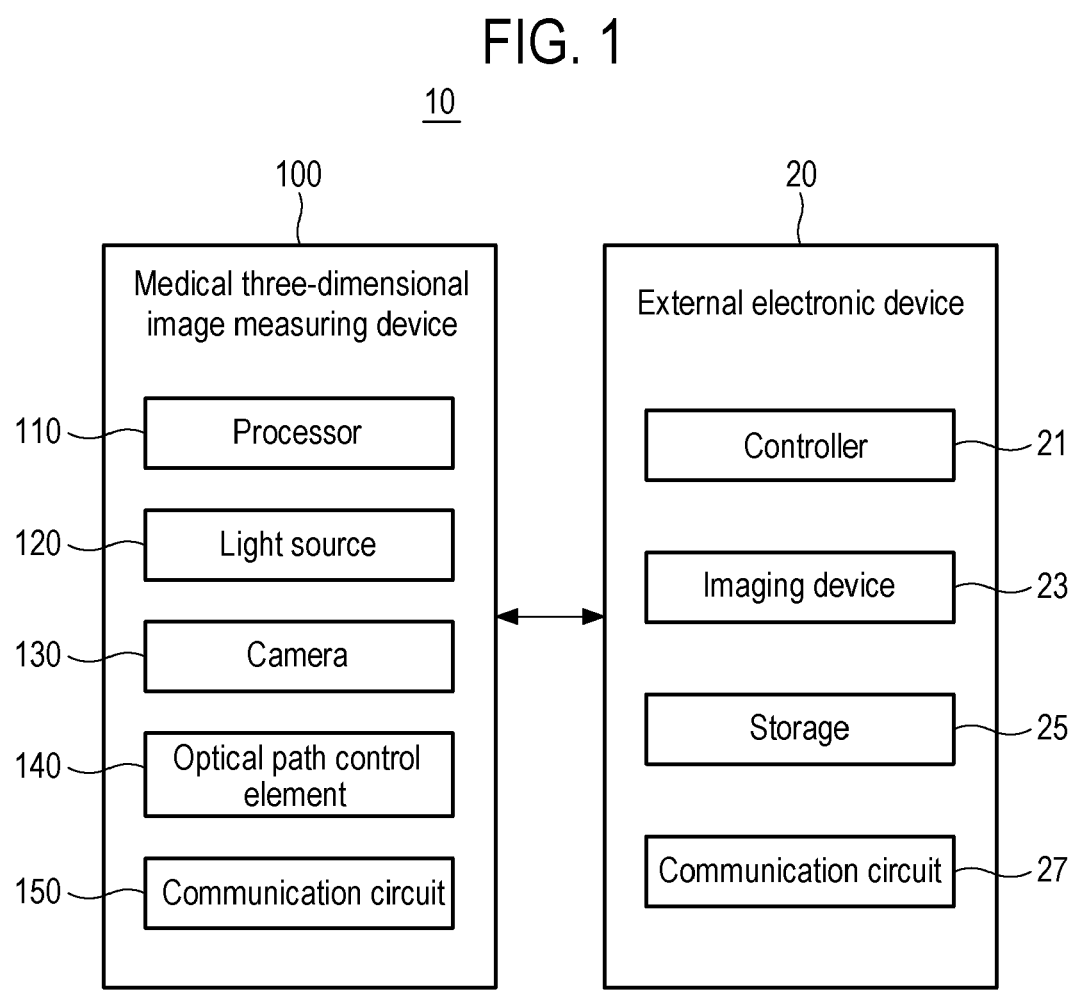

| Medical three-dimensional image measuring device | External electronic device |
|---|---|
| 110 — Processor | Controller — 21 |
| 120 — Light source | Imaging device — 23 |
| 130 — Camera | Storage — 25 |
| 140 — Optical path control element | Communication circuit — 27 |
| 150 — Communication circuit | |

MEDICAL THREE-DIMENSIONAL IMAGE MEASURING DEVICE AND MEDICAL IMAGE MATCHING SYSTEM

TECHNICAL FIELD

The present disclosure relates to a medical three-dimensional image measuring device and a medical image matching system.

This present disclosure is derived from research conducted as part of the WC300 project technology development support, which is a national research and development project.

[Project identification number: S2482672, Title of research project: Development of surgical navigation fusion head and neck surgery robot system with matching accuracy of 1 mm or less, Contribution rate: 1/1, Host organization: KohYoung Technology Inc., Research period: 2017 Mar. 1~2021 Dec. 31].

BACKGROUND

Recently, surgical navigation technology has been used to support doctors in surgical operations. By arranging markers on a surgical instrument and a medical three-dimensional image measuring device that photographs a patient's surgical site, respectively, and tracking the markers through an optical tracking system with an imaging device such as a camera, the location and posture of the surgical instrument can be tracked, and an image of the surgical site photographed through the medical three-dimensional image measuring device can be matched with a previously recorded patient's medical image (e.g., CT image or MRI image). Through this, the location and posture information of the surgical instrument on the patient's medical image can be recognized on the system.

The location information and posture information of the surgical instrument or the medical three-dimensional image measuring device on which the marker is arranged may be obtained using the image of the marker acquired through the optical tracking system. For example, the location information may be defined as spatial coordinates such as coordinates on the X, Y, and Z axes of the Cartesian coordinate system, and the posture information may be defined as roll, pitch, and yaw.

The medical three-dimensional image measuring device may measure a three-dimensional image of a patient's surgical site in order to acquire and process image information regarding the patient's surgical site. For example, the medical three-dimensional image measuring device uses a method of measuring a pattern generated by irradiating the surgical site with certain patterned light and acquiring a three-dimensional image of an object therefrom.

SUMMARY

When the medical three-dimensional image measuring device changes the location and/or posture to photograph the surgical site, there is a limitation in that the optical tracking system cannot change the location and/or posture of the medical three-dimensional image measuring device to a location and/or posture in which the marker of the medical three-dimensional image measuring device cannot be tracked. In the related art, depending on the patient's various surgical postures (e.g., parkbench posture, prone posture, and supine posture), the field of view of the optical tracking system is blocked due to interference by the patient or other objects (e.g., pedestal, surgical instrument, etc.), which may cause a problem that it is difficult to photograph the marker. Embodiments of the present disclosure solve the above-described problem of the related art.

According to an aspect of the present disclosure, a medical three-dimensional image measuring device includes a light source configured to output light, a camera configured to generate three-dimensional image information by receiving reflected light generated by reflecting the light from an object, a housing including the camera disposed therein and forming an opening through which the reflected light enters into the housing, and a marker disposed on the housing to be capable of changing at least one of a relative location or a relative posture to the opening and including a tracking surface configured to be imaged by an external imaging device for tracking a location and a posture.

According to another aspect of the present disclosure, a medical image matching system includes a medical three-dimensional image measuring device including a light source configured to output light, a camera configured to generate three-dimensional image information by receiving reflected light generated by reflecting the light from an object, a housing including the camera disposed therein and forming an opening through which the reflected light enters into the housing, and a marker disposed on the housing to be capable of changing at least one of a relative location or a relative posture to the opening and including a tracking surface configured to be imaged by an external imaging device for tracking a location and a posture, and an external electronic device including an imaging device for forming a tracking image by imaging at least a portion of the tracking surface of the marker, the external electronic device being configured to receive the three-dimensional image information and determine the location and the posture of the marker using the tracking image to determine coordinates of the three-dimensional image information.

According to the embodiments of the present disclosure, the location and/or posture of a marker can be changed so as not to block the field of view for the marker of the imaging device by a patient fixing device, a surgical instrument, a medical three-dimensional image measuring device itself, and/or an operator, so that tracking of the marker by the external electronic device can be performed smoothly.

According to the embodiments of the present disclosure, it is possible to improve convenience by reducing an operator's burden of not obscuring the field of view for the marker of the optical tracking system, and it is also possible to provide the operator with a condition that allows the operator to concentrate more on photographing the surgical site and manipulating the surgical instrument. For example, even in a difficult surgical condition where the patient's surgical posture is in a prone position and the surgical site is facing downward, the operator can change the location and/or posture of the marker of the medical three-dimensional image measuring device to easily secure the field of view for the marker of the optical tracking system.

According to the embodiments of the present disclosure, it is possible to change the location and/or posture of the marker so that the tracking of the marker of the medical three-dimensional image measuring device can be seamlessly performed.

BRIEF DESCRIPTION OF DRAWINGS

FIG. 1 is a block diagram showing a medical image matching system 10 according to one embodiment of the present disclosure.

FIG. 3 is a cross-sectional view of a medical three-dimensional image measuring device 100 according to one embodiment of the present disclosure.

FIG. 5 is a cross-sectional view of the medical three-dimensional image measuring device 101 of FIG. 4, which is taken along line S1-S1'.

DETAILED DESCRIPTION

Figure 2:
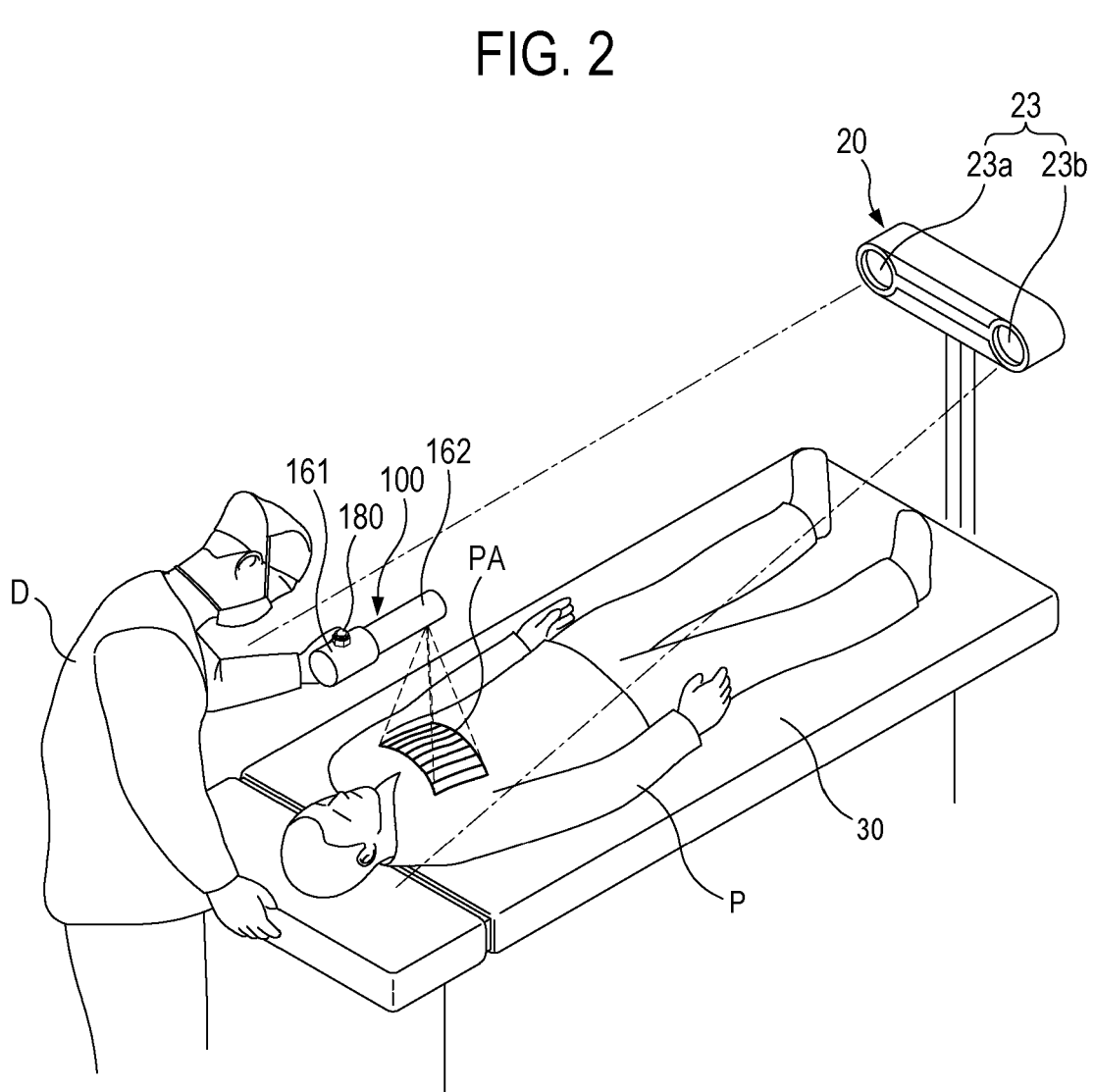
FIG. 2 is a view showing a state in which the medical image matching system 10 according to one embodiment of the present disclosure is used.

Embodiments of the present disclosure are illustrated for describing the technical spirit of the present disclosure. The scope of the claims according to the present disclosure is not limited to the embodiments described below or to the detailed descriptions of these embodiments.

All technical or scientific terms used herein have meanings that are generally understood by a person having ordinary knowledge in the art to which the present disclosure pertains, unless otherwise specified. The terms used herein are selected for only more clear illustration of the present disclosure, and are not intended to limit the scope of claims in accordance with the present disclosure.

The expressions "include," "provided with," "have" and the like used herein should be understood as open-ended terms connoting the possibility of inclusion of other embodiments, unless otherwise mentioned in a phrase or sentence including the expressions.

A singular expression can include meanings of plurality, unless otherwise mentioned, and the same is applied to a singular expression stated in the claims.

The terms "first," "second," etc. used herein are used to identify a plurality of components from one another, and are not intended to limit the order or importance of the relevant components.

When a certain component is described as "coupled to" or "connected to" another component, this should be understood as having a meaning that the certain component may be coupled or connected directly to the other component or that the certain component may be coupled or connected to the other component via a new intervening component.

Hereinafter, embodiments of the present disclosure will be described with reference to the accompanying drawings. In the accompanying drawings, identical or corresponding components are indicated by like reference numerals. In the following description of embodiments, repeated descriptions of the identical or corresponding components will be omitted. However, even if a description of a component is omitted, such a component is not intended to be excluded in an embodiment.

Figure 3:
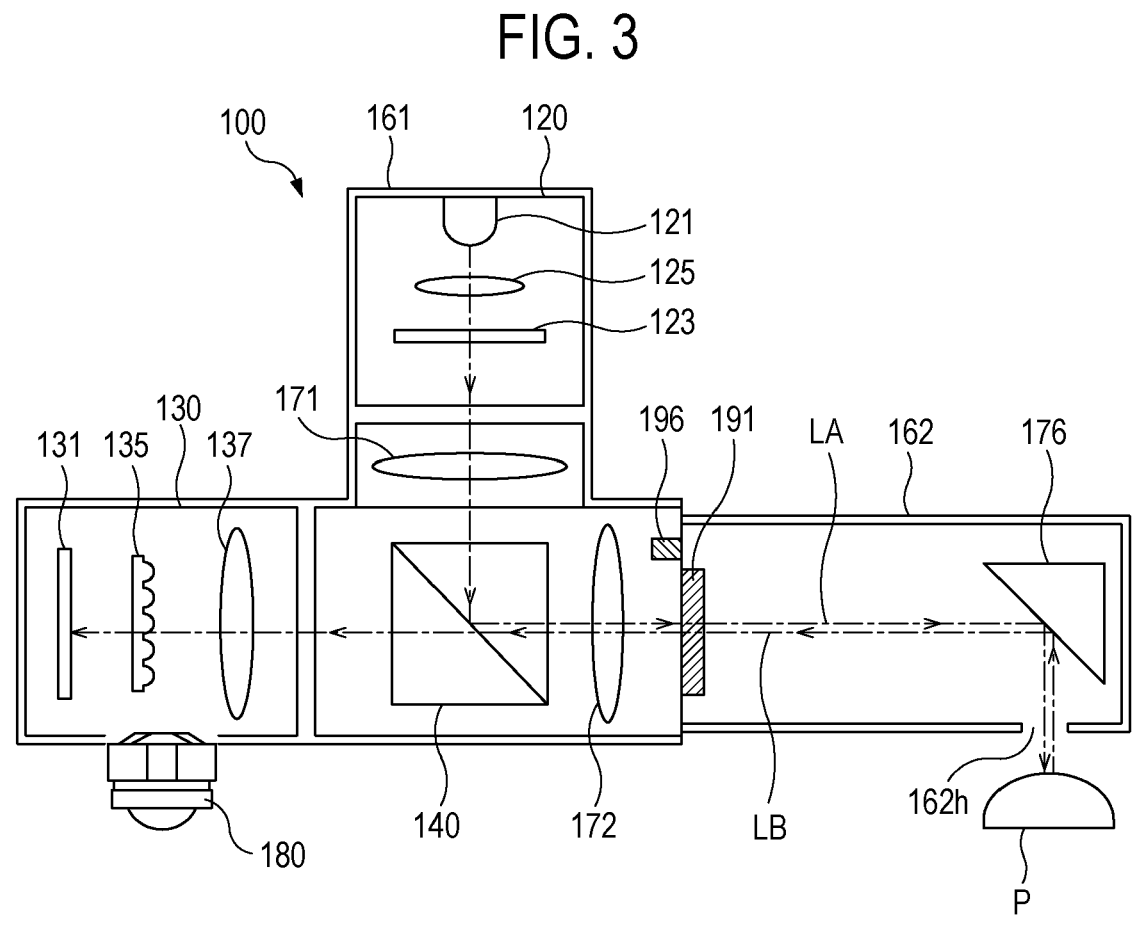

FIG. 1 is a block diagram showing a medical image matching system 10 according to one embodiment of the present disclosure. FIG. 2 is a view showing a state in which the medical image matching system 10 according to one embodiment of the present disclosure is used. FIG. 3 is a cross-sectional view of a medical three-dimensional image measuring device 100 according to one embodiment of the present disclosure.

Referring to FIGS. 1 to 3, the medical image matching system 10 may include a medical three-dimensional image measuring device 100 and an external electronic device 20. The medical three-dimensional image measuring device 100 and the external electronic device 20 may communicate with each other to transmit/receive various data (e.g., images). Even if some of the components shown in FIG. 1 are omitted or replaced, there will be no problem in implementing various embodiments disclosed in the present disclosure.

The medical three-dimensional image measuring device 100 may include a processor 110. The processor 110 may perform calculations or data processing related to control and/or communication of other components of the medical three-dimensional image measuring device 100. The processor 110 may process signals received from other components of the medical three-dimensional image measuring device 100. The processor 110 may control the medical three-dimensional image measuring device 100 to send signals to the external electronic device 20. The processor 110 may load commands or data received from other components of the medical three-dimensional image measuring device 100 into a memory (not shown), process the commands or data stored in the memory, and output the resulting data.

The medical three-dimensional image measuring device 100 may include a light source 120. The light source 120 may output patterned light. An object (e.g., a patient) P may be irradiated with the patterned light output from the light source 120. The patterned light may be light having a specific pattern or light having a pattern with a constant or specific period in order to capture a three-dimensional image of the object P. The patterned light may include, for example, patterned light in the form of random dots, patterned light in the form of a checkered pattern, patterned light in which the brightness of stripes is in the form of a sine wave, patterned light in the form of on-off with repeated bright and dark portions, and triangular wave patterned light in which a change in brightness is a triangular waveform. However, the shape of the patterned light is not limited thereto.

The light source 120 may include a pattern unit in which a plurality of patterns are formed, and an LED that irradiates the pattern unit with light. The light source 120 may include a condensing lens 125 configured to condense the light output from the LED 121 and irradiate the pattern unit with the condensed light. The light output from the LED 121 may reflect the patterns by passing through the pattern unit 123 in which the plurality of patterns are formed. The LED 121 may emit infrared light, for example, but is not limited thereto.

The medical three-dimensional image measuring device 100 may include a camera 130. The camera 130 may be a component that captures an image of the object P. The camera 130 may acquire three-dimensional image data of the object P by photographing the object, and may acquire a three-dimensional image of the object P by processing the acquired image data.

For example, the camera 130 may acquire the image of the object P by photographing the object P irradiated with the patterned light. The processor 110 may generate the three-dimensional image of the object P based on a phase shift method using the patterned light. For example, when the object P is irradiated with the patterned light having a certain shape through the light source 120, the intensity of light appearing on the surface of the object P may vary according to the curvature of the surface of the object. The processor 110 may generate the three-dimensional image by generating phase data from the image generated through camera 130.

In one embodiment, the camera 130 may be a light field camera 130 that generates a light field image. The light field camera 130 may be configured to determine a depth of the object P posteriorly after photographing the object, and to combine images having different depths of the object P. An image sensor of the light field camera 130 may have a posterior and variable depth of the object P. The camera 130 may generate the light field image of the object P in which the pattern is reflected. The processor 110 may generate a three-dimensional image of the surface of the object P by generating phase data from the light field image and calculating a height of each point constituting the surface of the object P.

The camera 130 may include a condensing lens 137, a lens array 135, and an image sensor 131. The condensing lens 137 may condense light entering from the object P. The lens array 135 may be a lens in which a plurality of micro lenses are arranged. The image sensor 131 may capture light passing through the lens array 135 and generate a light field image using the captured light. The image sensor 131 may be divided into regions corresponding to the respective ones of the plurality of micro lenses. The image sensor 131 may include, for example, a charge-coupled device (CCD) sensor or a complementary metal-oxide semiconductor (CMOS) sensor.

The light field image generated by the camera 130 according to one embodiment may include a plurality of sub-images that store color information and direction information of light together. For example, when the object P is irradiated with patterned light and reflected light reflected from the object P is received by the camera 130, the light field image may be an image in which a plurality of sub-images including color information and direction information of the reflected light are combined. The camera 130 may perform a refocusing process using the plurality of sub-images included in the light field image. For example, in the refocusing process, the camera 130 may generate an image of a desired depth by combining the depth of a desired object P and information of pixels corresponding to the optical path and direction backward calculated accordingly, among pixels of the light field image. For example, the camera 130 may generate an image in which all regions of the object P are in focus during the refocusing process. In order for the camera 130 to form an image of an accurate photographing target region, a distance between the medical three-dimensional image measuring device 100 and the photographing target region of the object P needs to be adjusted. When using the camera 130 that generates the light field image, since the depth of the object P can be determined posteriorly and a focused light field image can be generated for all regions of the object, there is no need to adjust the focal length in advance. In the case of the camera 130 generating the light field image, a measurable depth range is wider than that of the camera 130 using a general lens, so that a three-dimensional image of the object P can be acquired with a single shot.

The medical three-dimensional image measuring device 100 may include an optical path control element 140. The optical path control element 140 may reflect the patterned light in a specific direction so that the object P is irradiated with the patterned light output from the light source 120. The optical path control element 140 may transmit the reflected light reflected from the object P to reach the camera 130. The optical path control element 140 may be, for example, a transflective mirror. As one example, the light source 120 and the camera 130 may be disposed perpendicular to each other with respect to the optical path control element 140.

The medical three-dimensional image measuring device 100 may include housings 161 and 162 forming the appearance thereof. The housings 161 and 162 may include the first housing 161 and the second housing 162 coupled to each other. The second housing 162 may be coupled to the first housing 161 in a relatively movable manner. A marker 180 may be disposed on the first housing 161.

The camera 130 is disposed inside the housings 161 and 162. An opening 162h through which the reflected light inflows is formed in the housings 161 and 162. A lens (not shown) made of a light-transmissive material may be disposed in the opening 162h. The light source 120 may be disposed inside the housings 161 and 162. The optical path control element 140 may be disposed inside the housings 161 and 162.

In an embodiment disclosed in FIG. 3, the light source 120, the camera 130, and the optical path control element 140 are disposed inside the first housing 161 and the opening 162h is formed in the second housing 162 so that the object P is irradiated with the patterned light output from the light source 120, but the present disclosure is not limited thereto. In another embodiment, the light source 120, the camera 130, and the optical path control element 140 may be disposed in the second housing 162 and the opening 162h may be formed in the second housing 162.

In one embodiment, a user may use the medical three-dimensional image measuring device 100 while holding the first housing 161 or the second housing 162. The first housing 161 or the second housing 162 may include a component (e.g., a handle) that facilitates a user's movement, carrying, and use of the medical three-dimensional image measuring device 100.

In another embodiment, the first housing 161 or the second housing 162 may be supported by another external device (e.g., an operating table 30 or a stand (not shown) fixed to the floor, etc.). The stand may be configured to change the location and posture of the medical three-dimensional image measuring device 100.

The medical three-dimensional image measuring device 100 may be configured to transmit information to the external electronic device 20 through wireless or wired communication. The medical three-dimensional image measuring device 100 may include a communication circuit 150. The communication circuit 50 may be configured to transmit information to the external electronic device 20. The communication circuit 150 may establish a communication channel with the external electronic device 20 and transmit/receive various data to/from the external electronic device According to one embodiment, the communication circuit 150 may include a cellular communication module and be configured to be connected to a cellular network (e.g., 3G, LTE, 5G, Wibro, or Wimax). According to another embodiment, the communication circuit 150 may include a short-range communication module to transmit/receive data to/from the external electronic device by using short-range communication (e.g., Wi-Fi, Bluetooth, Bluetooth Low Energy (BLE), or UWB). The medical three-dimensional image measuring device 100 may further include wired communication lines 151, 152, and 153 for transmitting/receiving information to/from the external electronic device 20 (see FIGS. 4 to 10).

In one embodiment, the processor 110 may generate a three-dimensional image of the surface of the object P using the light field image of the object P acquired through the camera 130. For example, the light intensity of the emitted patterned light appearing on the surface of the actual photographing target region may vary according to the curvature of the surface of the photographing target region of the object P. The processor 110 may use the light field image of the object P to measure the light intensity that varies according to the curvature of the surface of the object P, generate phase data from the measured light intensity, and calculate the height of each point constituting the surface. The processor 110 may generate a three-dimensional image of the surface of the object P by calculating the height of each point constituting the surface of the object P. The processor 110 may transmit the three-dimensional image of the surface of the object P to the external electronic device 20 through the communication circuit 150.

The external electronic device 20 may include a controller 21. The controller 21 may perform calculations or data processing related to control and/or communication of other components of the external electronic device 20. The controller 21 may process signals received from other components of the external electronic device 20. The processor 110 may perform a process to send signals received from the medical three-dimensional image measuring device 100. The controller 21 may load received commands or data into a memory (not shown), process the commands or data stored in the memory, and output the resulting data.

The external electronic device 20 may include an imaging device 23. The imaging device 23 may image at least a portion of a tracking surface of the marker 180 attached to the medical three-dimensional image measuring device 100 to form a tracking image of at least the portion of the tracking surface. For example, the tracking surface may be a pattern surface, and in this case the tracking image is a pattern image. The imaging device 23 may include, for example, at least two or more cameras 23a and 23b capable of forming an image of at least a portion of the marker. The external electronic device 20 may determine the location and/or posture of the marker 180 using the formed tracking image.

In an embodiment in which the marker 180 includes the pattern surface as the tracking surface, when the pattern image of the marker 180 is acquired, the external electronic device 20 may extract at least one among sub-patterns from the pattern image, as a basic unit constituting the pattern of the marker 180. The location of at least one extracted sub-pattern within the entire pattern may be determined, and the posture of the marker 180 may be determined based on the determined location of the sub-pattern within the entire pattern. Here, the posture of the marker 180 may mean a three-dimensional direction or orientation of the marker 180 relative to the imaging device 23. For example, the location of the marker 180 or the medical three-dimensional image measuring device 100 may be determined using triangulation based on two images having a stereoscopic relationship among images formed by the imaging device 23 including at least two cameras 23a and 23b. When the location and posture of the marker 180 are determined as described above, the location and posture of the medical three-dimensional image measuring device 100 to which the marker 180 is attached may be determined based on the geometric relationship between the marker 180 and the medical three-dimensional image measuring device 100 to which the marker 180 is attached.

The external electronic device 20 may include a storage 25. The storage 25 may store various data used by at least one component (e.g., the controller 21) of the external electronic device 20. For example, the controller 21 may cause the storage 25 to store the three-dimensional image of the surface of the object P received from the medical three-dimensional image measuring device 100. For example, the controller 21 may cause the storage 25 to store medical images (e.g., CT images and MRI images) received from a medical device (not shown).

The external electronic device 20 may transmit/receive information to/from the medical three-dimensional image measuring device 100 through wireless or wired communication. The external electronic device 20 may include a communication circuit 27. The communication circuit 27 of the external electronic device 20 may establish a communication channel with the medical three-dimensional image measuring device 100 and transmit/receive information to/from the medical three-dimensional image measuring device 100. According to one embodiment, the communication circuit 27 of the external electronic device 20 may include a cellular communication module and be configured to be connected to a cellular network (e.g., 3G, LTE, 5G, Wibro, or Wimax). According to another embodiment, the communication circuit 27 of the external electronic device 20 may include a short-range communication module to transmit/receive data to/from the medical three-dimensional image measuring device 100 by using short-range communication (e.g., Wi-Fi, Bluetooth, Bluetooth Low Energy (BLE), or UWB). The external electronic device 20 may further include a wired communication line (not shown) for transmitting/receiving information to/from the medical three-dimensional image measuring device 100.

The controller 21 may perform image matching between the image of the surface of the object P received from the medical three-dimensional image measuring device 100 and the medical image of the object P. The image of the surface of the object P generated by the medical three-dimensional image measuring device 100 may be the external surface of a target included in the medical image or a portion thereof. For example, if the medical image is an image modeling the three-dimensional shape of a head of the object P, the three-dimensional image of the surface of the object P may be an image obtained by measuring the external shapes of the eyes, nose, mouth, ears, etc. on the surface of the head of the object P.

In one embodiment, the three-dimensional image of the surface of the object P may have a unique coordinate system (e.g., x1y1z1 coordinate system) of the medical three-dimensional image measuring device 100. The coordinate system of the three-dimensional image of the surface of the object P may be different from the coordinate system of the medical image (e.g., x2y2z2 system) and the coordinate system of the external electronic device 20 (e.g., x0y0z0 system). The coordinate system of the external electronic device 20 may mean, for example, the coordinate system of the imaging device 23 of the external electronic device 20.

Referring to FIG. 2, a user (e.g., a doctor) D may acquire a three-dimensional image of the surface of the object P using the medical three-dimensional image measuring device 100. For example, the user D may use the medical three-dimensional image measuring device 100 to irradiate the surface of the object P with patterned light. A pattern PA may be formed on the surface of the object P by the patterned light with which the surface of the object is irradiated.

In one embodiment, the medical three-dimensional image measuring device 100 may generate a light field image of the object P by receiving reflected light reflected from the object P. The light field image of the object P may be, for example, an image in which a plurality of sub-images of the formed pattern PA are combined. The medical three-dimensional image measuring device 100 may generate a three-dimensional image of the surface of the object P by using the light field image of the object P. The medical three-dimensional image measuring device 100 may transmit the generated three-dimensional image of the surface of the object P to the external electronic device 20.

The external electronic device 20 may image at least a portion of a tracking surface of the marker 180 attached to the medical three-dimensional image measuring device 100 through the imaging device to form a tracking image of at least the portion of the tracking surface. The external electronic device 20 may determine the location and posture of the medical three-dimensional image measuring device 100 to which the marker 180 is attached, based on the formed tracking image.

The external electronic device 20 may transform the coordinate system of the three-dimensional image of the surface of the object P into the coordinate system of the external electronic device 20. For example, the external electronic device 20 may transform the coordinate system of the three-dimensional image of the surface of the object P into the coordinate system of the external electronic device 20 based on the location and posture of the medical three-dimensional image measuring device 100 determined through the marker 180.

The external electronic device 20 may transform the coordinate system of the medical image of the object P received from the medical device into the coordinate system of the external electronic device 20. The external electronic device 20 according to various embodiments may perform image matching by unifying the coordinate systems between the three-dimensional image of the surface of the object P and the medical image of the object P.

Referring to FIG. 3, the medical three-dimensional image measuring device 100 may include at least one condensing lens 171 or 172 for condensing light. The condensing lenses 171 and 172 may be disposed on an optical path. The condensing lenses 171 and 172 may be disposed around the optical path control element 140. The at least one condensing lens 171 or 172 may include a first condensing lens 171 disposed on a path of light from the light source 120 toward the optical path control element 140. The at least one condensing lens 171 or 172 may include a second condensing lens 172 disposed on a path of light from the optical path control element 140 toward the object P.

The medical three-dimensional image measuring device 100 may include the light source 120 that outputs light. The light source 120 may include the LED 121. The light source 120 may include the pattern unit 123 in which a plurality of patterns are formed. The pattern unit 123 may be irradiated with the light output from the LED 121. The light source 120 may include the condensing lens 125 configured to condense the light output from the LED 121 and radiate the pattern unit 123 with the light between the pattern unit 123 and the LED 121. The light output from the LED 121 may reflect the pattern by passing through the pattern unit 123. According to one embodiment, the light output from the light source 120 may be incident to the optical path control element 140. The light incident to the optical path control element 140 may be reflected in a direction in which a reflective mirror 176 is disposed so that the object P can be irradiated with the light. In another embodiment not shown, the medical three-dimensional image measuring device may not include the optical path control element 140 and the light output from the light source 120 may be directly incident toward the reflective mirror 176.

In one embodiment, the light may be reflected by the reflective mirror 176 and the object P may irradiated with the light through the opening 162$h$ of the second housing 162. In another embodiment not shown, the medical three-dimensional image measuring device does not include the reflective mirror 176 and the object P may be irradiated with the light through an opening formed on an optical path LA without being reflected by the reflective mirror 176.

The medical three-dimensional image measuring device 100 may be configured so that the optical path LA of light output from the light source 120 and emitted to the object P and an optical path LB of reflected light reflected from the object P and reaching the camera 130 are coaxial. The optical path LA and the optical path LB may coaxially overlap in a section between the optical path control element 140 and the object P.

The light with which the object P is irradiated may be reflected by the object P. The reflected light reflected from the object P may be incident again into the second housing 162 through the opening 162$h$. In one embodiment, the reflected light may be reflected by the reflective mirror 176 and incident to the optical path control element 140. In another embodiment not shown, the medical three-dimensional image measuring device does not include the reflective mirror 176 and the reflected light may be directly incident to the optical path control element 140 without additional reflection.

The reflected light incident to the optical path control element 140 may pass through the optical path control element 140 and reach the camera 130. In another embodiment not shown, the medical three-dimensional image measuring device does not include the optical path control element 140 and the reflected light may be directly incident to the camera 130.

The medical three-dimensional image measuring device 100 may include the camera 130 configured to generate image information by receiving the reflected light. The camera 130 may include the condensing lens 137 through which the reflected light passes. The camera 130 may include the lens array 135 in which a plurality of micro lenses through which the reflected light passes are arranged. The camera 130 may include the image sensor 131 that captures the reflected light. The reflected light may pass through the condensing lens 137 and the lens array 135 and reach the image sensor 131.

For example, the image sensor 131 may generate a light field image of the object P by capturing the reflected light. The light field image of the object P may be an image of a pattern formed on the object P. The processor 110 may generate a three-dimensional image of the surface of the object P using the light field image. The processor 110 may transmit the three-dimensional image of the surface of the object P to the external electronic device 20 through the communication circuit 150.

The medical three-dimensional image measuring device 100 may include the marker 180 including a tracking surface. The marker 180 is disposed in the housings 161 and 162. The marker 180 may be disposed in the first housing 161.

The marker 180 is disposed in the housings 161 and 162 to be capable of changing at least one of a position relative to the opening 162h and a posture relative to the opening 162h. Specifically, the marker 180 may be fixed to the first housing 161, and the second housing 162 may be coupled to the first housing 161 to be capable of changing at least one of a position relative to the first housing 161 and a posture relative to the first housing 161. The opening 162h may be formed in the second housing 162.

In one embodiment, the marker 180 may include a pattern surface (not shown) on which a pattern is formed, as the tracking surface. The marker 180 may include a lens (not shown) configured to identify at least a portion of a uniquely appearing pattern from the outside of the marker 180 according to a direction viewed from the outside of the marker 180. The lens of the marker 180 may be a ball lens. The pattern surface may include a recessed curved shape.

The external electronic device 20 is configured to receive the image information generated by the camera 130 of the medical three-dimensional image measuring device 100. The external electronic device 20 may include the communication circuit 27 for receiving the image information.

The external electronic device 20 may include the imaging device 23 for forming a tracking image by shooting at least a portion of the tracking surface of the marker 180. The external electronic device 20 may be configured to determine the location and posture of the marker 180 using the tracking image to determine the coordinates of the image information.

In one embodiment, the external electronic device 20 may determine the location or coordinate and posture or orientation of the medical three-dimensional image measuring device 100 to which the marker 180 is attached, based on the formed pattern image. The location of the medical three-dimensional image measuring device 100 may be defined by spatial coordinates such as coordinates on the x, y, and z axes of the Cartesian coordinate system. The posture of the medical three-dimensional image measuring device 100 may be defined as roll, pitch, and yaw. The external electronic device 20 may capture an image of the marker 180 attached to the medical three-dimensional image measuring device 100 through the imaging device 23, thereby tracking the location and posture of the medical three-dimensional image measuring device 100.

For example, the imaging device 23 of the external electronic device 20 may form a pattern image of at least a portion of a pattern visually identified from the outside of the marker 180 through the ball lens of the marker 180. When the pattern image of at least the portion of the pattern surface is acquired, the external electronic device 20 may process information extracted from the pattern image of at least the portion of the pattern surface to determine the location and posture of the marker 180. The external electronic device 20 may determine the location and posture of the medical three-dimensional image measuring device 100 to which the marker 180 is attached, based on the location and posture of the marker 180. A specific method of calculating the location and posture of the marker 180 using the image of at least the portion of the pattern surface may be the same as one among known optical tracking methods.

The medical three-dimensional image measuring device 100 may be configured to be capable of changing at least one of relative location and relative posture of the marker 180 to the opening 162h into which the reflected light is introduced.

The medical three-dimensional image measuring device 100 may include a sensor 196 for detecting displacement information according to a change in at least one of the relative location and the relative posture of the marker 180 to the opening. The communication circuit 150 may be configured to transmit the displacement information of the marker 180 to the external electronic device 20.

The external electronic device 20 may receive the displacement information of the marker 180. The external electronic device 20 may be configured to determine the coordinates of the image information generated in the medical three-dimensional image measuring device 100, based on the displacement information. For example, the external electronic device 20 may correct the position or posture of the medical three-dimensional image measuring device 100 based on the displacement information, and information on the corrected position or posture of the medical three-dimensional image measuring device 100 may be used for matching images between the image information (image information generated by the medical three-dimensional image measuring device) and the medical image (e.g., CT image or MRI image).

The image information may have a unique coordinate system (e.g., x1y1z1 coordinate system) of the medical three-dimensional image measuring device 100. The coordinate system of the image information may be different from the coordinate system (e.g., x2y2z2) of the medical image and may be different from the coordinate system (e.g., x0y0z0) of the external electronic device 20.

The medical image matching system 10 may transform the coordinate system (e.g., x2y2z2) of the medical image and the coordinate system (e.g., x1y1z1) of the image information into the coordinate system (e.g., x0y0z0) of the external electronic device 20. The external electronic device 20 may perform matching between the medical image and the image information, which have different coordinate systems. In order to perform matching between the medical image and the image information, the external electronic device 20 may extract a surface image from the medical image and perform matching between the extracted surface image and the received image information. Here, the surface image extracted from the medical image may have the same coordinate system (e.g., x2y2z2) of the medical image. In addition, the external electronic device 20 may transform the coordinate system (e.g., x1y1z1) of the image information into the coordinate system (e.g., x0y0z0) of the external electronic device 20 by mediation of the marker 180 attached to the medical three-dimensional image measuring device 100. In addition, the medical image and the surface image extracted from the medical image may also be transformed into the coordinate system (e.g., x0y0z0) of the external electronic device 20. The external electronic device 20 may perform the matching between the image information and the medical image using various image matching algorithms. For example, the external electronic device 20 may perform matching using an interactive closest point (ICP) algorithm.

The second housing 162 may be configured to be capable of changing relative location and/or posture to the first housing 161 by being disposed to be capable of being moved relative to the first housing 161. Here, the meaning of relative movement includes that the second housing 162 is moving with respect to the first housing 161 and the first housing 161 is moving with respect to the second housing 161. This enables any one of the relative location and the relative posture of the marker 180, which is fixed to the first housing 161, to the opening 162h to be changed.

The marker 180 is configured to be capable of changing at least one of the relative location and the relative posture to the opening 162h by performing at least one of (i) relative translational motion to the opening 162h and (ii) relative rotational motion to the opening 162h around a predetermined axis of rotation. The second housing 162 is configured to be capable of changing at least one of the relative location and the relative posture of the marker 180 to the opening 162h by performing at least one of (i) relative translational motion to the first housing 161 and (ii) relative rotational motion to the first housing 161 around a predetermined axis of rotation. The 'axis of rotation' used herein is a virtual axis that does not refer to the actual parts of the device. The meaning of 'relative translational motion of a component A to a component B' used herein includes the translational motion of the component A with respect to the component B and the translational motion of the component B with respect to the component A. In addition, the meaning of 'relative rotational motion of a component C to a component D around a predetermined axis of rotation' used herein includes the rotational motion of the component C with respect to the component D around the predetermined axis of rotation and the rotational motion of the component D with respect to the component C around the predetermined axis of rotation.

As one example, the marker 180 may be configured to be capable of performing the relative translational motion to the opening 162h. Specifically, the marker 180 may be translated relative to the opening 162h, and the opening 162h may be translated relative to the marker 180. Here, the second housing 162 may be configured to be capable of performing the relative translational motion to the first housing 161. Accordingly, a distance between the marker 180 and the opening 162h may be changed. For example, in third, fourth, and sixth embodiments to be described later with reference to FIGS. 7, 8, and 10, respectively, the marker 180 may perform the relative translational motion to the opening 162h.

As another example, the marker 180 may perform the relative rotational motion to the opening 162h around a predetermined axis of rotation. Specifically, the marker 180 may be rotated relative to the opening 162h around the predetermined axis of rotation, and the opening 162h may be rotated relative to the marker 180 about the predetermined axis of rotation. Here, the second housing 162 may be configured to be capable of performing the relative rotational motion to the first housing 161 around the predetermined axis of rotation. Accordingly, the distance and/or posture of the marker 180 to the opening 162h may be changed. For example, in first, second, fifth, and sixth embodiments to be described later with reference to FIGS. 4, 5, 6, 9, and 10, respectively, the marker 180 may be rotated relative to the opening 162h around a predetermined axis of rotation.

In one embodiment with reference to FIG. 3, the second housing 162 may be rotatably coupled to the first housing 161. The medical three-dimensional image measuring device 100 may include a bearing 191 interposed between the first housing 161 and the second housing 162 so that the second housing 162 can be relatively rotated with respect to the first housing 161. The second housing 162 may be rotated with respect to the first housing 161 based on the central axis of the bearing 191.

The sensor 196 may detect the displacement information according to a change in at least one of the relative location and the relative posture of the first housing 161 to the second housing 162. The sensor 196 may employ any one of various sensors and may be implemented with two or more types of sensors.

In one embodiment, the sensor 196 may detect rotation angle information about rotation of the second housing 162 relative to the first housing 161. That is, when the second housing 162 is rotated with respect to the first housing 161 or the first housing 161 is rotated with respect to the second housing 162, the sensor 196 detects the rotation angle information. For example, the sensor 196 may be a gyro sensor or an encoder. Such a sensor may be applied to the first, second, fifth, and sixth embodiments to be described later with reference to FIGS. 4, 5, 6, 9, and 10, respectively.

In another embodiment, the sensor 196 may detect distance information about a relatively moved distance of the second housing 162 with respect to the first housing 161. That is, when the second housing 162 is moved relative to the first housing 161 or when the first housing 161 is moved relative to the second housing 162, the sensor 196 can detect the distance information. For example, the sensor 196 may be an infrared sensor, a 3D sensor, an ultrasonic sensor, an RF sensor, a geomagnetic sensor, an encoder, and the like. Such a sensor may be applied to the third, fourth, and sixth embodiments to be described later with reference to FIGS. 7, 8, and 10, respectively.

The processor 110 may transmit the displacement information to the external electronic device 20 through the communication circuit 150. In one embodiment, the processor 110 may transmit the rotation angle information to the external electronic device 20 through the communication circuit 150. In another embodiment, the processor 110 may transmit the distance information to the external electronic device 20 through the communication circuit 150.

Figure 4:
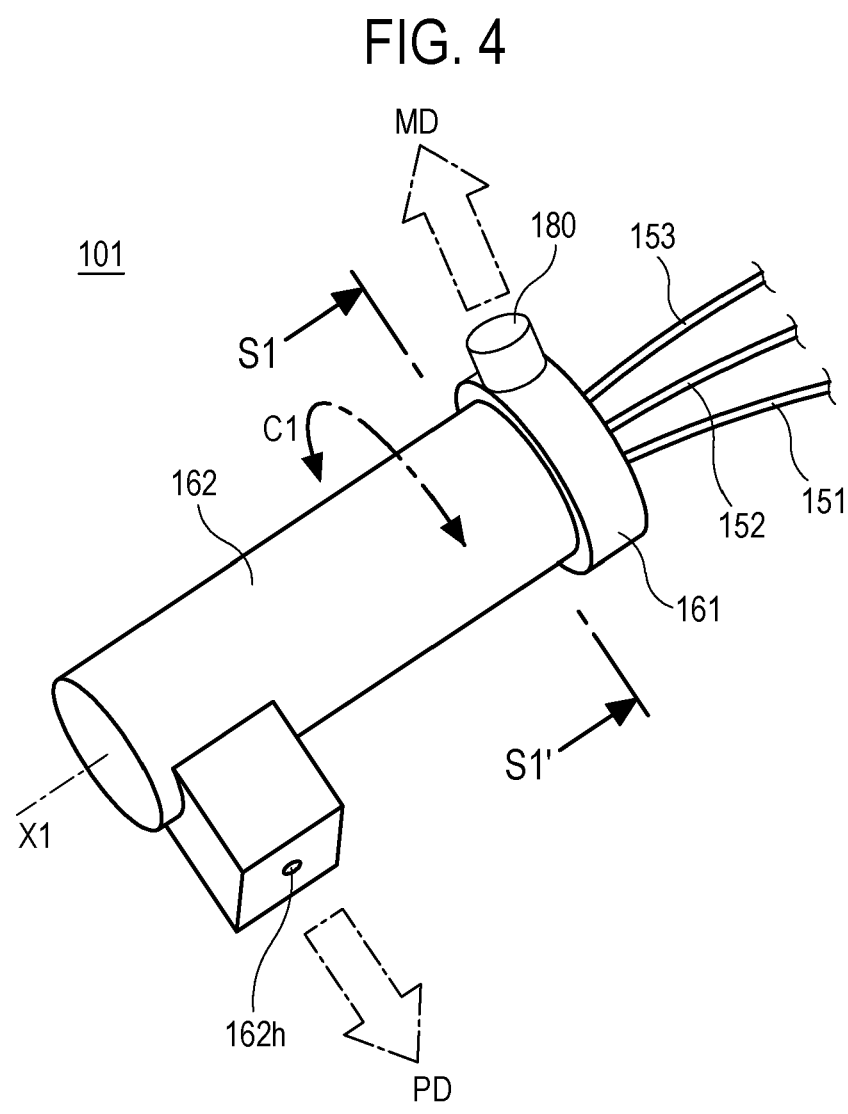
FIG. 4 is a perspective view of a medical three-dimensional image measuring device 101 according to a first embodiment of the present disclosure.
Figure 5:
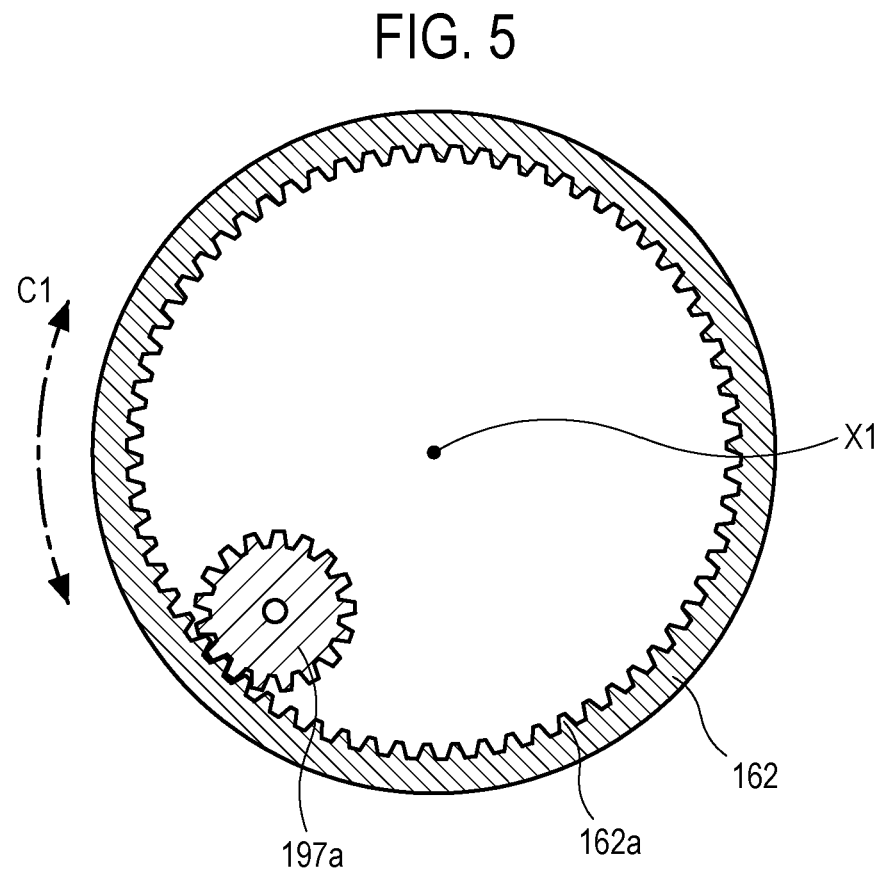

FIG. 4 is a perspective view of a medical three-dimensional image measuring device 101 according to the first embodiment of the present disclosure. FIG. 5 is a cross-sectional view of the medical three-dimensional image measuring device 101 of FIG. 4, which is taken along line S1-S1'. Hereinafter, the medical three-dimensional image measuring device 101 according to the first embodiment will be described, focusing on differences from the above-described embodiments of the medical three-dimensional image measuring device 100. A direction PD in which light is emitted through the opening 162h and a direction MD in which the marker 180 is viewed from the front are shown in the figure.

Referring to FIGS. 4 and 5, the second housing 162 of the medical three-dimensional image measuring device 101 is configured to be capable of changing the relative posture to the first housing 161 by being arranged to be capable of being rotated relative to the first housing 161 around a predetermined axis of rotation X1. A rotational direction C1 of the rotational motion is shown in the figures.

The rotation axis X1 may extend parallel to a path LB of the reflected light immediately before reaching the camera 130 (see FIG. 3). For example, the rotation axis X1 may coincide with the optical path LB. This enables the position of the optical path LB to be maintained even when the first housing 161 and the second housing 162 are rotated relative to each other. A sensor (not shown) of the medical three-dimensional image measuring device 101 may be configured to detect rotation angle information according to a change in the relative posture of the second housing 162.

The medical three-dimensional image measuring device 101 may include a first communication line 151 configured to transmit the rotation angle information to the external electronic device 20. The medical three-dimensional image measuring device 101 may include a second communication line 152 configured to transmit the image information generated by the camera 130 to the external electronic device 20. The medical three-dimensional image measuring device 101 may include a third communication line 153 configured to transmit trigger information for synchronizing the image information generated by the camera 130 and the image captured by the imaging device 23 of the external electronic device 20 to the external electronic device 20.

The medical three-dimensional image measuring device 101 may be configured to automatically perform the rotational motion. For example, the medical three-dimensional image measuring device 101 may include a motor (not shown) for generating a driving force and gears 197a and 162a to which the driving force is transmitted. A driven gear 162a may be formed in the second housing 162. For example, the driven gear 162a may be a ring gear formed along the rotational direction C1 on the inner wall surface of the second housing 162. A driving gear 197a may be rotated in engagement with the driven gear 162a to transmit the driving force to the driven gear 162a.

Figure 6:
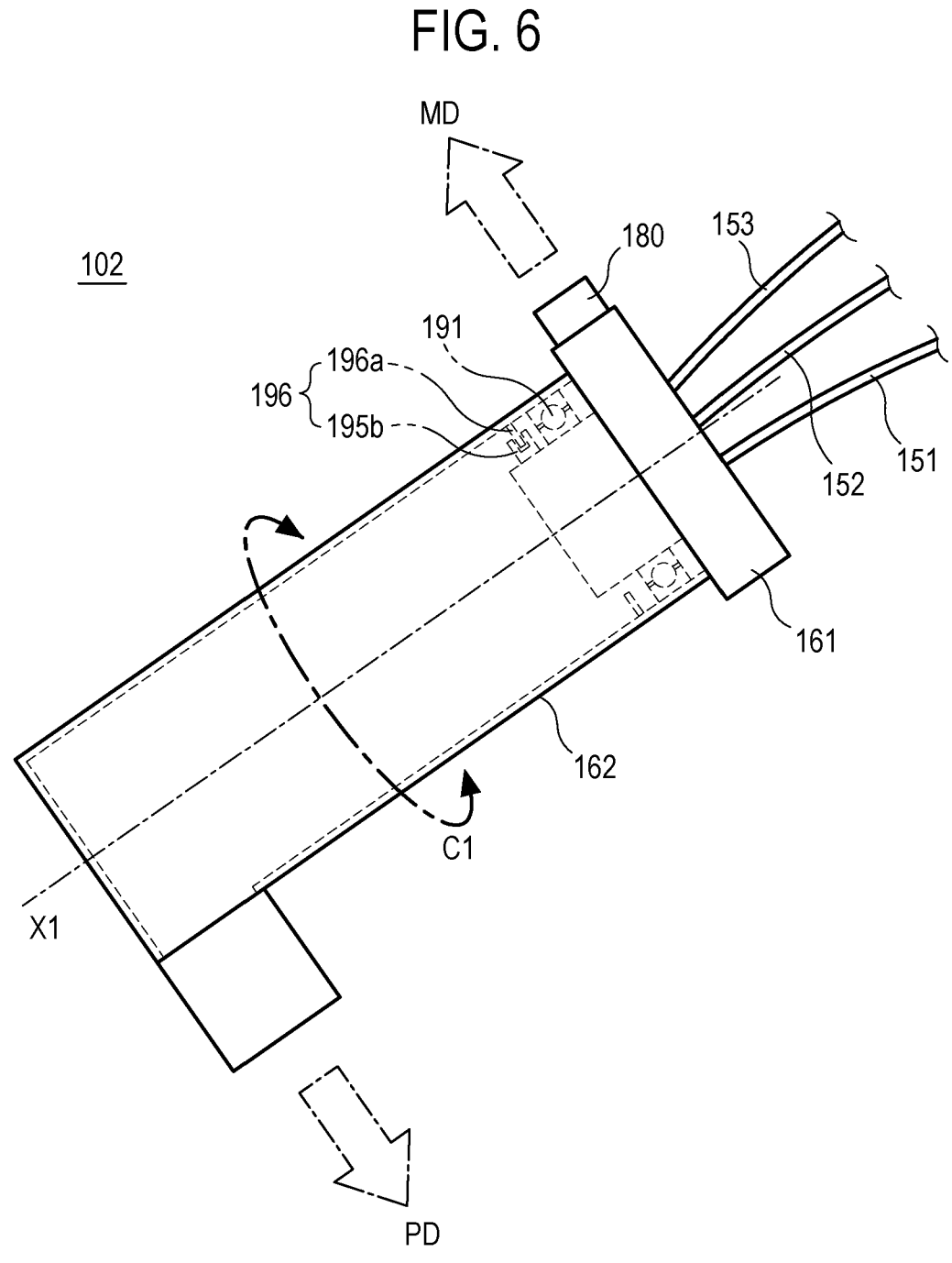
FIG. 6 is an elevational view of a medical three-dimensional image measuring device 102 according to a second embodiment of the present disclosure.

FIG. 6 is an elevational view of a medical three-dimensional image measuring device 102 according to the second embodiment of the present disclosure. Hereinafter, the medical three-dimensional image measuring device 102 according to the second embodiment will be described, focusing on differences from the above-described medical three-dimensional image measuring device 101 according to the first embodiment.

Referring to FIG. 6, the medical three-dimensional image measuring device 102 may be configured such that the rotation motion is manually performed by a user. The medical three-dimensional image measuring device 102 includes a bearing 191 interposed between the first housing 161 and the second housing 162 so that the second housing 162 can be relatively rotated with respect to the first housing 161. For example, the bearing 191 may be a ball bearing.

A sensor 196 of the medical three-dimensional image measuring device 101 may be configured to detect the rotation angle information according to a change in the relative posture of the second housing 162. For example, the sensor 196 may include an encoder. The encoder may include a target unit 196a formed on one of the first housing 161 and the second housing and a sensing unit 196b formed on the other. The target unit 196a may extend along the rotational direction C1 around the rotation axis X1. The sensing unit 196b may be disposed to face a specific position of the target unit 196a, and the specific position may be changed according to the rotational motion. The rotation angle information may be detected through information on the specific position of the target unit 196a detected by the sensing unit 196b.

Figure 7:
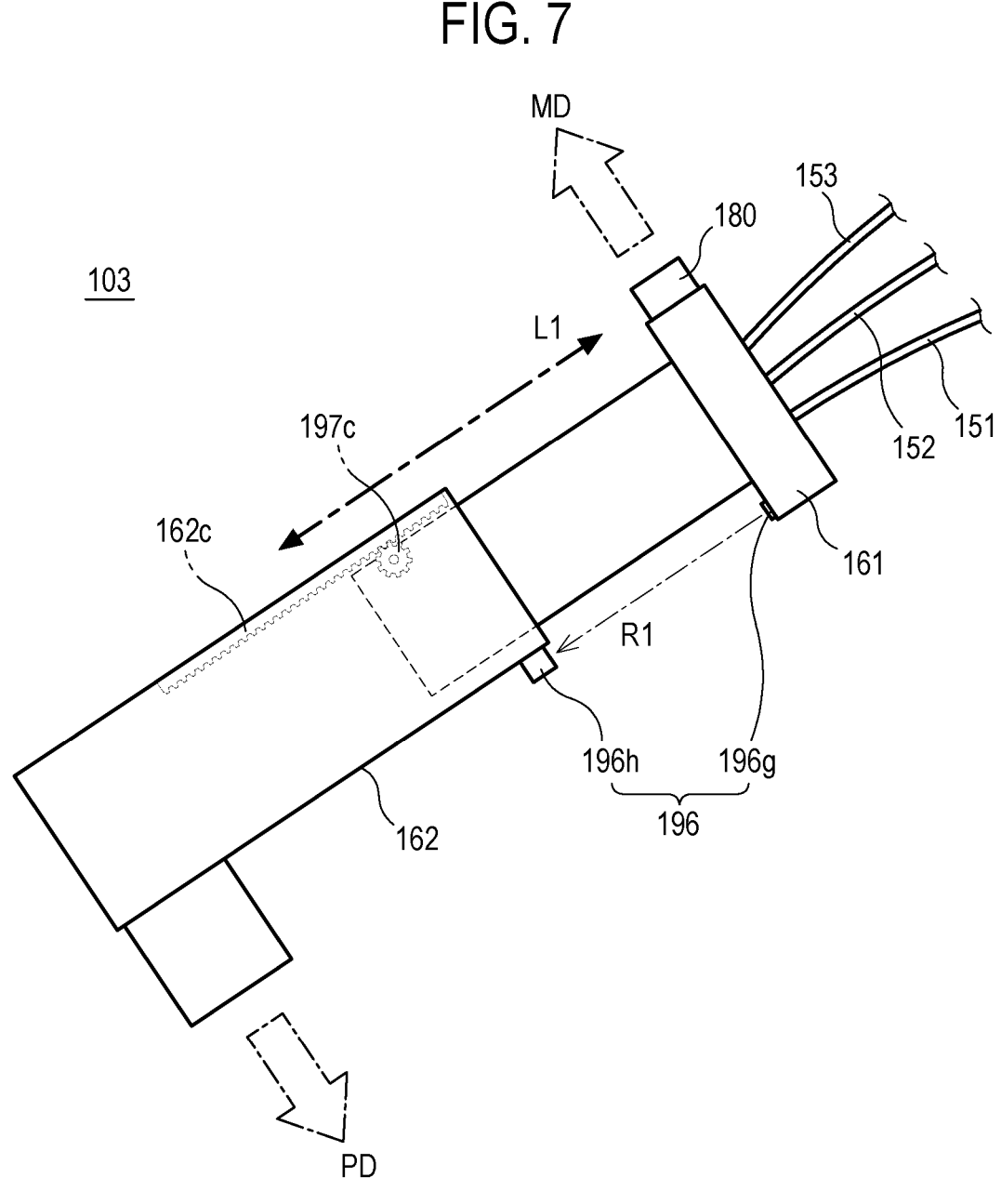
FIG. 7 is an elevational view of a medical three-dimensional image measuring device 103 according to a third embodiment of the present disclosure.

FIG. 7 is an elevational view of a medical three-dimensional image measuring device 103 according to a third embodiment of the present disclosure. Hereinafter, the medical three-dimensional image measuring device 103 according to the third embodiment will be described, focusing on differences from the above-described medical three-dimensional image measuring devices 101 and 102 according to the first and second embodiments.

Referring to FIG. 7, the second housing 162 of the medical three-dimensional image measuring device 103 is configured to be capable of changing the relative location to the first housing 161 by being disposed to be capable of translating relative to the first housing 161. A movement direction L1 of the translational motion is shown in the figure.

The medical three-dimensional image measuring device 103 includes a sensor 196 configured to detect distance information about a relatively moved distance of the second housing 162 with respect to the first housing 161 according to a change in the relative location of the second housing 162. For example, the sensor 196 may be an infrared sensor. The sensor 196 may include a light emitting unit 196g that emits an infrared ray R1, and a light receiving unit 196h that senses the infrared ray R1 and generates the distance information. The first communication line 151 may be configured to transmit the distance information to the external electronic device 20.

The medical three-dimensional image measuring device 103 may be configured to automatically perform the translational motion. For example, the medical three-dimensional image measuring device 103 may include a motor (not shown) for generating a driving force and gears 197c and 162c to which the driving force is transmitted. A driven gear 162c may be formed in the second housing 162. For example, the driven gear 162c may be a rack formed on the inner wall surface of the second housing 162 along the movement direction L1, and a driving gear 197c may be a pinion. The driving gear 197c may be rotated in engagement with the driven gear 162c to transmit the driving force to the driven gear 162a.

Figure 8:
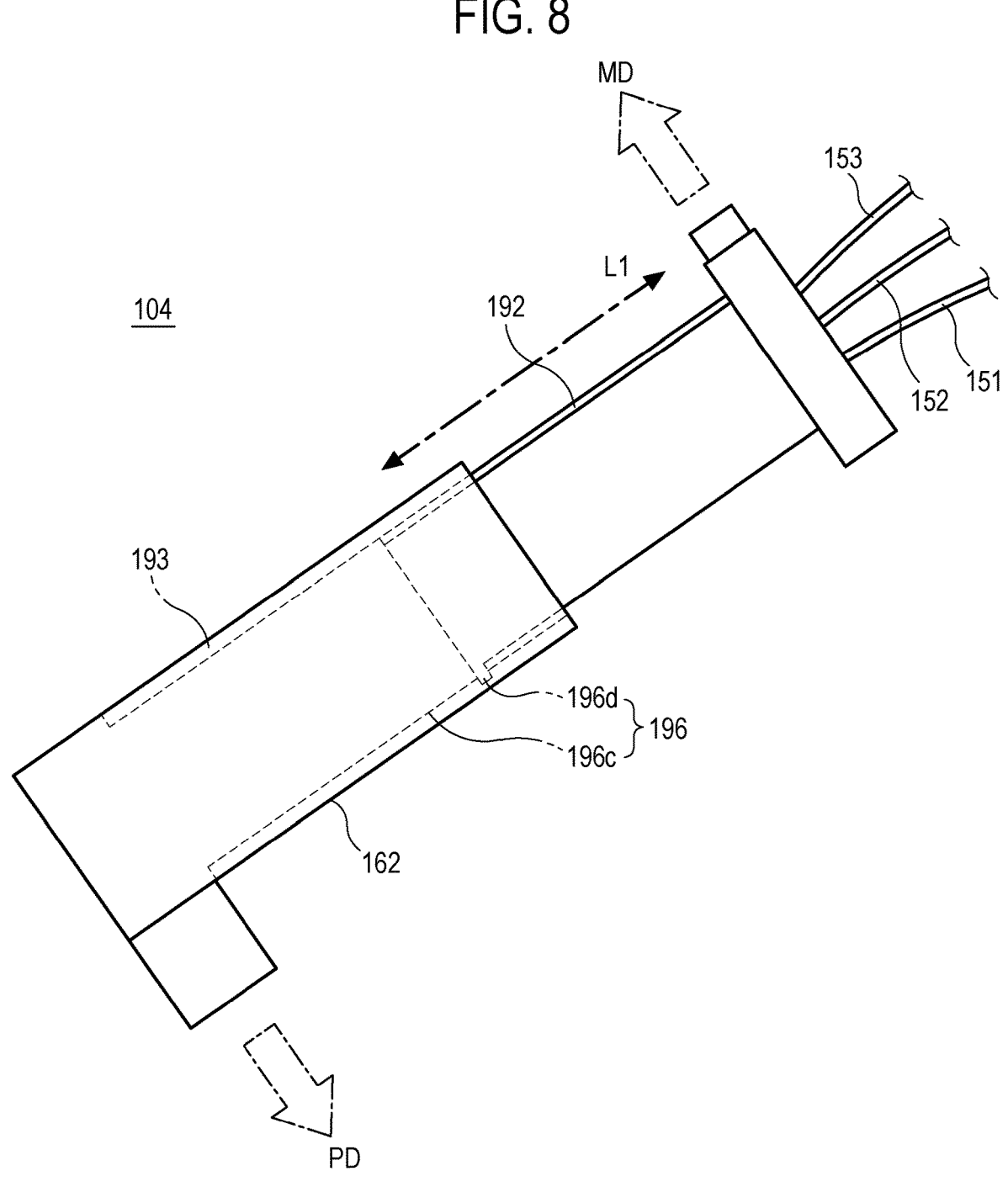
FIG. 8 is an elevational view of a medical three-dimensional image measuring device 104 according to a fourth embodiment of the present disclosure.

FIG. 8 is an elevational view of a medical three-dimensional image measuring device 104 according to a fourth embodiment of the present disclosure. Hereinafter, the medical three-dimensional image measuring device 104 according to the fourth embodiment will be described, focusing on differences from the above-described medical three-dimensional image measuring device 103 according to the third embodiment.

Referring to FIG. 8, the medical three-dimensional image measuring device 104 may be configured such that the translational motion is manually performed by a user. The medical three-dimensional image measuring device 104 includes a slider 192 formed on one of the first housing 161 and the second housing 162, and a guide 193 formed on the other. The guide 193 is formed to extend along the movement direction (L1). The slider 192 may slide along the guide 193 and move in the movement direction L1.

The medical three-dimensional image measuring device 104 may include a sensor 196 configured to detect distance information about a relatively moved distance of the second housing 162 with respect to the first housing 161 according to a change in the relative location of the second housing 162. For example, the sensor 196 may include a linear encoder. The linear encoder may include a target unit 196c formed on one of the first housing 161 and the second housing and a sensing unit 196d formed on the other. The target unit 196c may extend along the movement direction C1. The sensing unit 196d may be disposed to face a specific position of the target unit 196c, and the specific position may be changed according to the translational motion. The distance information may be detected through information on the specific position of the target unit 196c detected by the sensing unit 196d.

Figure 9:
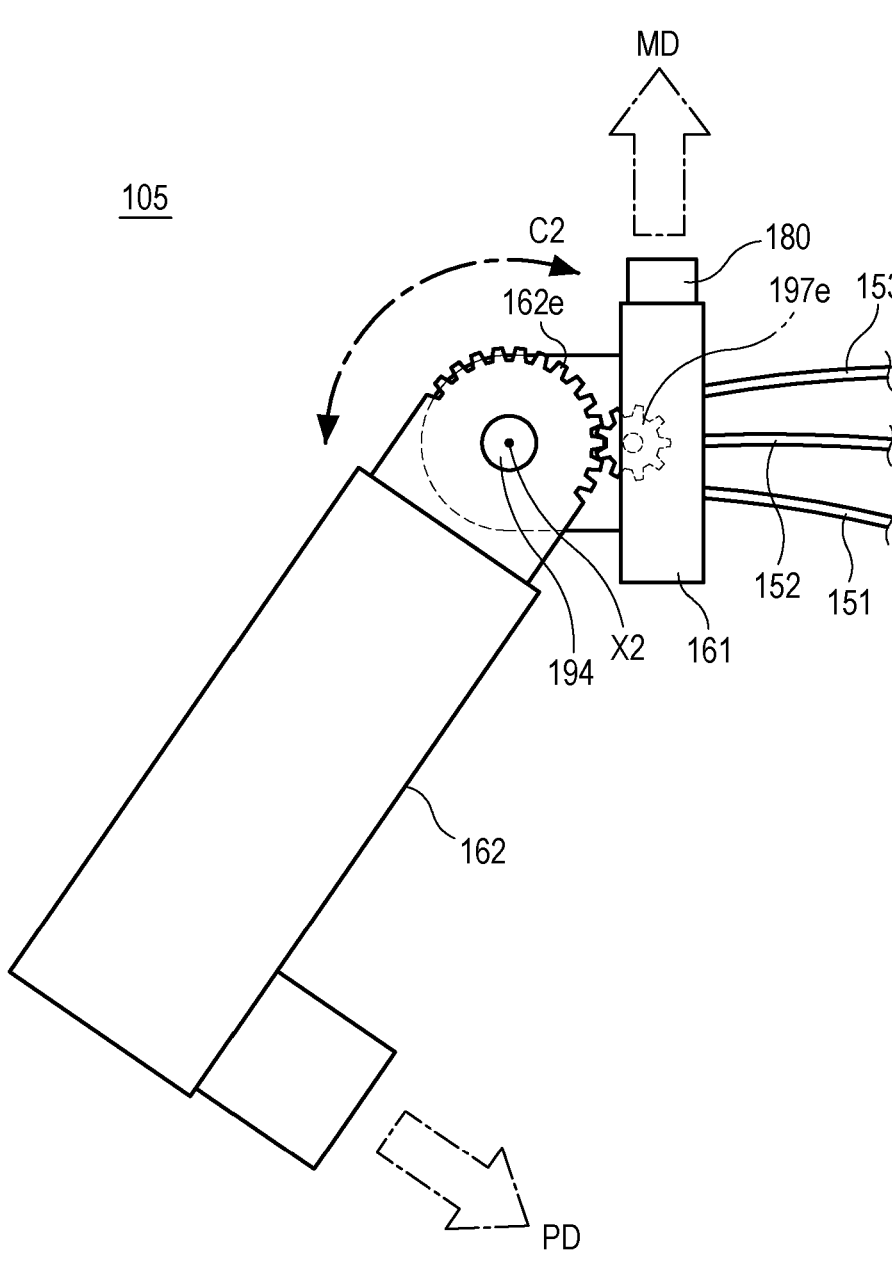
FIG. 9 is an elevational view of a medical three-dimensional image measuring device 105 according to a fifth embodiment of the present disclosure.

FIG. 9 is an elevational view of a medical three-dimensional image measuring device 105 according to a fifth embodiment of the present disclosure. Hereinafter, the medical three-dimensional image measuring device 105 according to the fifth embodiment will be described, focusing on differences from the above-described medical three-dimensional image measuring devices 101, 102, 103, and 104 according to the first to fourth embodiments.

Referring to FIG. 9, the second housing 162 of the medical three-dimensional image measuring device 105 is configured to be capable of changing the relative posture to the first housing 161 by being disposed to be capable of rotating relative to the first housing 161 around a predetermined rotation axis X2. A rotational direction C2 of the rotational motion is shown in the figure. The medical three-dimensional image measuring device 105 includes a hinge 194 configured to allow the rotational motion of the first housing 161 and the second housing 162 relative to each other. The hinge 194 may be disposed on the rotation axis X2.

The rotation axis X2 may extend in a direction crossing a path LB of the reflected light immediately before reaching the camera 130. In the medical three-dimensional image measuring device 105, the light source 120, the camera 130, and the optical path control element 140 may be disposed inside the second housing 162.

The medical three-dimensional image measuring device 105 may be configured to automatically perform the rotational motion. For example, the medical three-dimensional image measuring device 105 may include a motor (not shown) for generating a driving force, and gears 197e and 162e to which the driving force is transmitted. A driven gear 162e may be formed in the second housing 162. For example, the driven gear 162e may be formed around the periphery of the hinge 194. A driving gear 197e may be rotated in engagement with the driven gear 162e to transmit the driving force to the driven gear 162e.

Figure 10:
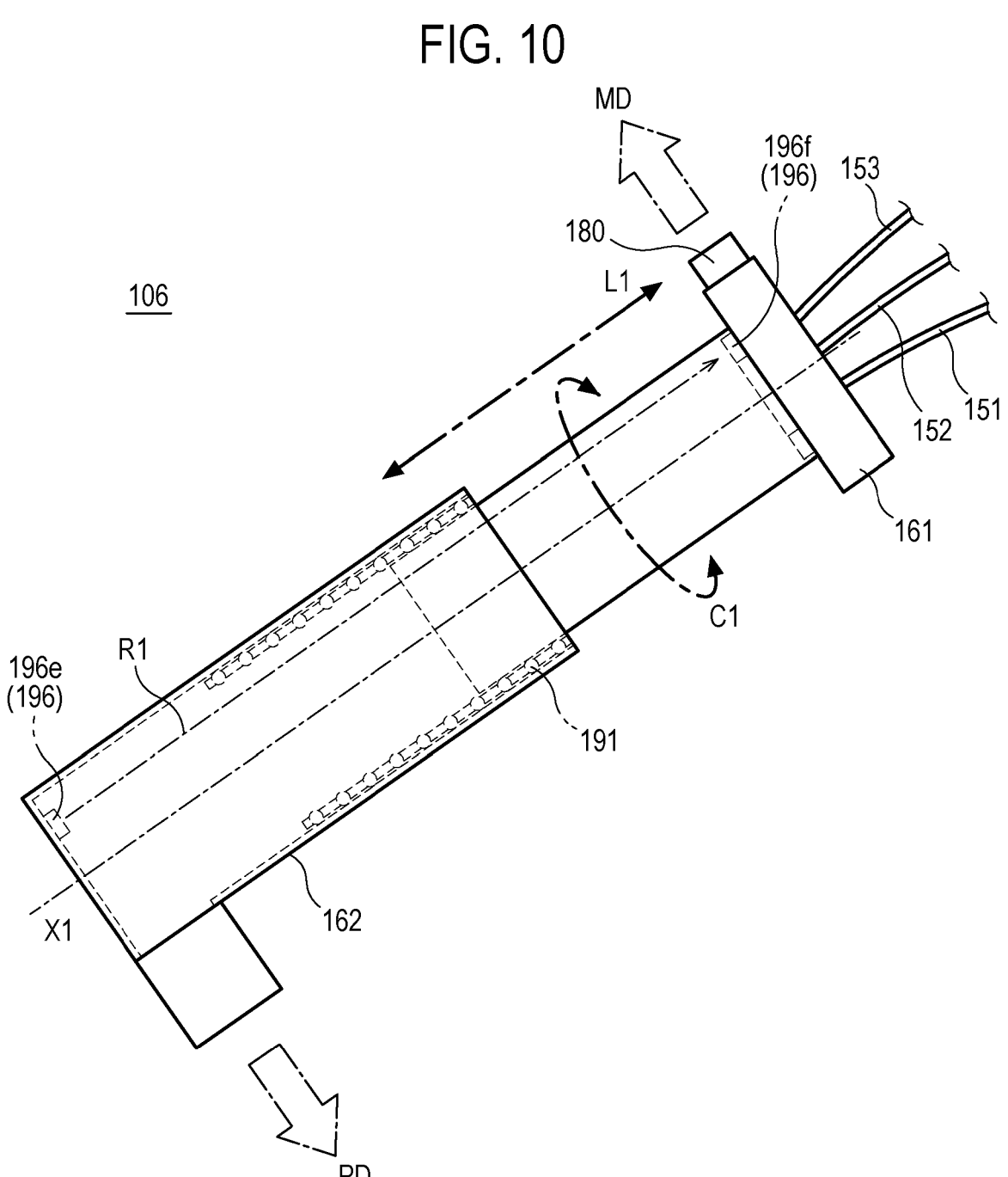
FIG. 10 is an elevational view of a medical three-dimensional image measuring device 106 according to a sixth embodiment of the present disclosure.

FIG. 10 is an elevational view of a medical three-dimensional image measuring device 106 according to a sixth embodiment of the present disclosure. Hereinafter, the medical three-dimensional image measuring device 106 according to the sixth embodiment will be described, focusing on differences from the above-described medical three-dimensional image measuring devices 101, 102, 103, 104, and 105 according to the first to fifth embodiments.

Referring to FIG. 10, the second housing 162 of the medical three-dimensional image measuring device 106 is configured to be capable of changing the relative location and posture to the first housing 161 by being disposed to be capable of rotating relative to the first housing 161 around a rotation axis X1 and translating relative to the first housing 161. A rotational direction C1 of the rotational motion and a movement direction L1 of the translational motion are shown in the figure.

The medical three-dimensional image measuring device 106 may be configured such that the rotational motion and the translational motion are manually performed by a user. The medical three-dimensional image measuring device 106 includes a bearing 191 interposed between the first housing 161 and the second housing 162 so that the second housing 162 can be relatively rotated and relatively translated with respect to the first housing 161. For example, the bearing 191 may be a ball bearing. The bearing 191 may be disposed on the inner wall surface of the second housing 162.

The sensor 196 of the medical three-dimensional image measuring device 106 may be configured to detect distance information about a relatively moved distance of the second housing 162 with respect to the first housing 161 according to a change in the relative location of the second housing 162 and detect rotation angle information according to a change in the relative posture of the second housing 162. For example, the sensor 196 may be an infrared sensor. The sensor 196 may include a light emitting unit 196e that emits an infrared ray R1, and a light receiving unit 196f that senses the infrared ray R1 and generates the distance information.

A plurality of light receiving units 196f may be arranged along the rotational direction C1, and the rotation angle information may be generated according to which a light receiving unit 196f among the plurality of light receiving units 196f detects the infrared ray R1.

Although the technical concept of the present disclosure has been described by the examples described in some embodiments and illustrated in the accompanying drawings, it should be noted that various substitutions, modifications, and changes can be made without departing from the scope of the present disclosure which can be understood by those skilled in the art to which the present disclosure pertains. In addition, it should be noted that that such substitutions, modifications, and changes are intended to fall within the scope of the appended claims.

What is claimed is:

1. A medical three-dimensional image measuring device comprising:
   a light source configured to output light;
   a camera configured to generate three-dimensional image information by receiving reflected light generated by reflecting the light from an object;
   a housing including the camera disposed therein and forming an opening through which the reflected light enters into the housing; and
   a marker disposed on the housing to be capable of changing at least one of a relative location or a relative posture to the opening and including a tracking surface configured to be imaged by an external imaging device for tracking a location and a posture,
   wherein the housing includes:
   a first housing to which the marker is fixed; and
   a second housing formed with the opening and coupled to the first housing to be capable of changing at least one of a relative location or a relative posture to the first housing.

2. The medical three-dimensional image measuring device of claim 1, wherein the light source is configured to output patterned light, and
   wherein the camera is configured to generate the three-dimensional image information by receiving the reflected light generated by reflecting the patterned light from the object.

3. The medical three-dimensional image measuring device of claim 1, further comprising:
   a sensor configured to detect displacement information according to a change in the at least one of the relative location or the relative posture of the marker to the opening; and
   a communication circuit configured to transmit the displacement information to an external electronic device.

4. The medical three-dimensional image measuring device of claim 1, wherein the marker is configured to be capable of changing the at least one of the relative location or the relative posture to the opening by performing at least one of (i) relative translational motion to the opening or (ii) relative rotational motion to the opening around a predetermined rotation axis.

5. The medical three-dimensional image measuring device of claim 1, wherein the second housing is configured to be capable of changing the at least one of the relative location or the relative posture of the marker to the opening by performing at least one of (i) relative translational motion to the first housing or (ii) relative rotational motion to the first housing around a predetermined rotation axis.

6. The medical three-dimensional image measuring device of claim 1, wherein the second housing is configured to be capable of changing the relative posture to the first housing by being disposed to be capable of rotating relative to the first housing around the predetermined rotation axis, the medical three-dimensional image measuring device further comprising:

a sensor configured to detect rotation angle information according to a change in the relative posture of the second housing.

7. The medical three-dimensional image measuring device of claim 6, further comprising: a bearing interposed between the first housing and the second housing so that the second housing is capable of relatively rotating with respect to the first housing.

8. The medical three-dimensional image measuring device of claim 6, wherein the second housing is configured to be capable of changing the relative location to the first housing by being disposed to be capable of translating relative to the first housing, and wherein the sensor is configured to detect distance information about a relatively moved distance of the second housing with respect to the first housing.

9. The medical three-dimensional image measuring device of claim 8, further comprising:

a bearing interposed between the first housing and the second housing so that the second housing is capable of translating and rotating relative to the first housing.

10. The medical three-dimensional image measuring device of claim 6, wherein the predetermined rotation axis extends parallel to a path of the reflected light immediately before reaching the camera.

11. The medical three-dimensional image measuring device of claim 6, wherein the predetermined rotation axis extends in a direction crossing a path of the reflected light immediately before reaching the camera.

12. The medical three-dimensional image measuring device of claim 1, wherein the second housing is configured to be capable of changing the relative location to the first housing by being disposed to be capable of translating relative to the first housing, the medical three-dimensional image measuring device further comprising:

a sensor configured to detect distance information about a relatively moved distance of the second housing with respect to the first housing according to a change in the relative location of the second housing.

13. The medical three-dimensional image measuring device of claim 12, further comprising:

a bearing interposed between the first housing and the second housing so that the second housing is capable of translating relative to the first housing.

14. A medical image matching system comprising:

a medical three-dimensional image measuring device including a light source configured to output light, a camera configured to generate three-dimensional image information by receiving reflected light generated by reflecting the light from an object, a housing including the camera disposed therein and forming an opening through which the reflected light enters into the housing, and a marker disposed on the housing to be capable of changing at least one of a relative location or a relative posture to the opening and including a tracking surface configured to be imaged by an external imaging device for tracking a location and a posture; and an external electronic device including an imaging device for forming a tracking image by imaging at least a portion of the tracking surface of the marker, the external electronic device being configured to receive the three-dimensional image information and determine the location and the posture of the marker using the tracking image to determine coordinates of the three-dimensional image information, wherein the housing includes:

a first housing to which the marker is fixed; and a second housing formed with the opening and coupled to the first housing to be capable of changing at least one of a relative location or a relative posture to the first housing.

15. The medical image matching system of claim 14, wherein the medical three-dimensional image measuring device further includes a sensor configured to detect displacement information according to a change in the at least one of the relative location or the relative posture of the marker to the opening, and wherein the external electronic device is configured to determine the coordinates of the three-dimensional image information based on the displacement information.

16. The medical image matching system of claim 14, further comprising:

a processor configured to:

cause the light source to output patterned light;

cause the camera to generate a light field image by receiving the reflected light generated by reflecting the patterned light from the object; and cause the medical three-dimensional image measuring device to generate a three-dimensional image of a surface of the object using the light field image.

\* \* \* \* \*